United States Patent
Jain et al.

(10) Patent No.: US 11,064,893 B2
(45) Date of Patent: Jul. 20, 2021

(54) REAL TIME AUTHENTICATION BASED ON BLOOD FLOW PARAMETERS

(71) Applicant: Samsung Electronics Co., Ltd., Suwon si (KR)

(72) Inventors: Jawahar Jain, Los Altos, CA (US); Vatche A. Attarian, San Jose, CA (US); Sajid Sadi, San Jose, CA (US); Pranav Mistry, Campbell, CA (US)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 228 days.

(21) Appl. No.: 15/654,263

(22) Filed: Jul. 19, 2017

(65) Prior Publication Data
US 2018/0020927 A1    Jan. 25, 2018

Related U.S. Application Data

(60) Provisional application No. 62/364,683, filed on Jul. 20, 2016.

(51) Int. Cl.
*A61B 5/117*    (2016.01)
*A61B 5/1455*    (2006.01)
(Continued)

(52) U.S. Cl.
CPC ............ *A61B 5/021* (2013.01); *A61B 5/0064* (2013.01); *A61B 5/0261* (2013.01);
(Continued)

(58) Field of Classification Search
CPC ... G06F 21/32; G06F 21/445; G07C 9/00158; G07C 9/25; G07C 9/37; A61B 3/1233;
(Continued)

(56) References Cited

U.S. PATENT DOCUMENTS 6,421,943 B1 * 7/2002 Caulfield ............. F41A 17/066
42/70.01
6,549,118 B1 * 4/2003 Seal .................. G06K 9/00597
340/5.52
(Continued)

FOREIGN PATENT DOCUMENTS

EP        3478175 A1    5/2019
KR    20150049550 A    5/2015
(Continued)

OTHER PUBLICATIONS

WIPO Appln. No. PCT/KR2017/007827, Written Opinion and International Search Report, dated Oct. 26, 2017, 13 pg.

(Continued)

*Primary Examiner* — Devin B Henson
*Assistant Examiner* — H. Q. Nguyen
(74) *Attorney, Agent, or Firm* — Cuenot, Forsythe & Kim, LLC

(57) ABSTRACT

Blood flow of a user can be measured using a sensor. Sensor data based on the measuring of the blood flow can be generated. Based on the sensor data, at least a first physiological biomarker of the blood flow measured by the sensor and at least a first morphological characteristic of the blood flow measured by the sensor can be determined. The user can be authenticated based, at least in part, on the first physiological biomarker and the first morphological characteristic.

15 Claims, 7 Drawing Sheets

(51) Int. Cl.

| | |
|---|---|
| *G06F 21/32* | (2013.01) |
| *H04L 9/32* | (2006.01) |
| *A61B 5/349* | (2021.01) |
| *G07C 9/37* | (2020.01) |
| *G06F 21/44* | (2013.01) |
| *A61B 5/024* | (2006.01) |
| *A61B 5/026* | (2006.01) |
| *G06K 9/00* | (2006.01) |
| *A61B 5/00* | (2006.01) |
| *A61B 5/021* | (2006.01) |
| *G16H 40/63* | (2018.01) |
| *H04L 29/06* | (2006.01) |
| *A61B 5/1172* | (2016.01) |

(52) U.S. Cl.
CPC .......... *A61B 5/02416* (2013.01); *A61B 5/117* (2013.01); *A61B 5/1455* (2013.01); *A61B 5/14551* (2013.01); *A61B 5/349* (2021.01); *A61B 5/6801* (2013.01); *A61B 5/681* (2013.01); *A61B 5/6897* (2013.01); *A61B 5/6898* (2013.01); *A61B 5/7246* (2013.01); *G06F 21/32* (2013.01); *G06F 21/445* (2013.01); *G06K 9/00885* (2013.01); *G06K 9/00892* (2013.01); *G07C 9/37* (2020.01); *G16H 40/63* (2018.01); *H04L 9/32* (2013.01); *H04L 9/3231* (2013.01); *H04L 9/3273* (2013.01); *H04L 63/0861* (2013.01); *H04L 63/0869* (2013.01); *A61B 5/1172* (2013.01); *G06K 2009/00939* (2013.01)

(58) Field of Classification Search
CPC ....... A61B 5/1455; A61B 5/117; A61B 5/026; A61B 5/02416; G06K 2009/00932; G06K 2009/00939; G06K 9/00885; G06K 9/00892; H04W 12/06; H04L 9/32; H04L 9/3231; H04L 9/3273; H04L 63/0853; H04L 63/0861; H04L 63/0869
See application file for complete search history.

(56) References Cited

U.S. PATENT DOCUMENTS

| | | | |
|---|---|---|---|
| 7,441,123 B2 * | 10/2008 | Grant ..................... | A61B 5/117 713/186 |
| 9,314,174 B1 | 4/2016 | Brady et al. | |
| 9,378,502 B2 | 6/2016 | Candelore et al. | |
| 9,396,643 B2 | 7/2016 | He et al. | |
| 9,419,956 B2 | 8/2016 | Abraham et al. | |
| 9,762,581 B1 * | 9/2017 | Wang .................. | H04L 63/0853 |
| 2007/0263906 A1 | 11/2007 | Hitoshi et al. | |
| 2009/0202113 A1 | 8/2009 | Hitoshi et al. | |
| 2010/0183812 A1 | 7/2010 | Shim et al. | |
| 2012/0148143 A1 | 6/2012 | Takiguchi | |
| 2012/0253154 A1 * | 10/2012 | Phillips ................ | G06K 9/0002 600/324 |
| 2013/0329031 A1 | 12/2013 | Miura et al. | |
| 2014/0249763 A1 * | 9/2014 | Shimuta ............... | A61B 5/6898 702/19 |
| 2015/0116086 A1 | 4/2015 | Kim et al. | |
| 2015/0119654 A1 | 4/2015 | Martin et al. | |
| 2015/0135310 A1 | 5/2015 | Lee | |
| 2015/0164351 A1 | 6/2015 | He et al. | |
| 2015/0190062 A1 | 7/2015 | Han et al. | |
| 2015/0288687 A1 * | 10/2015 | Heshmati ............... | G07C 9/257 726/7 |
| 2015/0312669 A1 | 10/2015 | Song et al. | |
| 2015/0332532 A1 | 11/2015 | Lee et al. | |
| 2016/0042167 A1 | 2/2016 | White et al. | |
| 2016/0058375 A1 | 3/2016 | Rothkopf | |
| 2016/0081627 A1 | 3/2016 | McGloin et al. | |
| 2016/0183812 A1 * | 6/2016 | Zhang .................. | A61B 5/7246 600/301 |
| 2016/0366590 A1 * | 12/2016 | Jun ........................ | H04W 12/06 |
| 2017/0011210 A1 * | 1/2017 | Cheong ................. | H04W 4/00 |
| 2017/0193208 A1 * | 7/2017 | Ashley .................... | G06F 21/32 |
| 2017/0227995 A1 * | 8/2017 | Lee ...................... | H04L 63/0892 |

FOREIGN PATENT DOCUMENTS

| | | |
|---|---|---|
| WO | 2015167926 A1 | 11/2015 |
| WO | 2018016891 A1 | 1/2018 |

OTHER PUBLICATIONS

"What is Windows Hello?" [online] Microsoft© 2017, Art. ID 17215, Apr. 11, 2017, Rev. 19, [retrieved Jul. 18, 2017], retrieved from the Internet: <https://support.microsoft.com/en-us/help/17215/windows-10-what-is-hello>, 3 pg.
"Touch ID," [online] Wikipedia, the free encyclopedia, Jul. 3, 2017, retrieved from the Internet: <"https://en.wikipedia.org/w/index.php?title=Touch_ID&oldid=788849067">, 6 pg.
EP Appln. 17831364.9, Extended European Search Report, dated Mar. 14, 2019, 9 pg.
Poon, C.C.Y. et al., "A Novel Biometrics Method to Secure Wireless Body Area Sensor Networks for Telemedicine and M-Heath," IEEE Communications Magazine, vol. 44, No. 4, Apr. 1, 2006, pp. 73-81.
EP Appln. No. 17831364.9, Communication Pursuant to Article 94(3) EPC, dated Dec. 9, 2019, 6 pg.

* cited by examiner

800

```
┌─────────────────────────────────────────────────────────────┐
│ Measure blood flow of a user and generate first sensor data │
│ based on the measuring of the blood flow                    │
│                         805                                 │
└─────────────────────────────────────────────────────────────┘
                              ↓
┌─────────────────────────────────────────────────────────────┐
│ Determine, based on the first sensor data, at least a first │
│ physiological biomarker of the blood flow measured by the   │
│ first sensor and at least a first morphological             │
│ characteristic of the blood flow measured by the first sensor│
│                         810                                 │
└─────────────────────────────────────────────────────────────┘
                              ↓
┌─────────────────────────────────────────────────────────────┐
│      Receive second sensor data generated by a second sensor│
│                         815                                 │
└─────────────────────────────────────────────────────────────┘
                              ↓
┌─────────────────────────────────────────────────────────────┐
│ Determine, based on the second sensor data, at least a      │
│ second physiological biomarker of a blood flow measured by  │
│ the second sensor and at least a second morphological       │
│ characteristic of the blood flow measured by the second sensor│
│                         820                                 │
└─────────────────────────────────────────────────────────────┘
                              ↓
┌─────────────────────────────────────────────────────────────┐
│ Compare at least the first physiological biomarker to at    │
│ least the second physiological biomarker and compare at     │
│ least the first morphological characteristic to at least    │
│ the second morphological characteristic                     │
│                         825                                 │
└─────────────────────────────────────────────────────────────┘
                              ↓
┌─────────────────────────────────────────────────────────────┐
│ Determine whether at least the first physiological biomarker│
│ matches at least the second physiological biomarker and     │
│ determine whether at least the first morphological          │
│ characteristic matches at least the second morphological    │
│ characteristic                                              │
│                         830                                 │
└─────────────────────────────────────────────────────────────┘
                              ↓
                     Yes   ╱ Match ╲   No
                    ┌─────<   835   >─────┐
                    │      ╲       ╱      │
                    ↓                     ↓
┌──────────────────────────┐   ┌──────────────────────────┐
│ Output an indicator      │   │ Output an indicator      │
│ indicating the user is   │   │ indicating the user is   │
│ authenticated            │   │ not authenticated        │
│         840              │   │         845              │
└──────────────────────────┘   └──────────────────────────┘
```

FIG. 8

REAL TIME AUTHENTICATION BASED ON BLOOD FLOW PARAMETERS

CROSS-REFERENCE TO RELATED APPLICATIONS

This application claims the benefit of Application No. 62/364,683 filed on Jul. 20, 2016, which is fully incorporated herein by reference.

TECHNICAL FIELD

This disclosure relates to user authentication.

BACKGROUND

User authentication is the verification of an active human-to-machine transfer of information required for confirmation of a user's authenticity. User authentication authorizes human-to-machine interactions. For example, user authentication may be used to authorize a user to use a client device, for example a computer, smart phone, etc., and/or to access network connected systems and resources. User authentication typically includes collecting information about a user and authenticating the user based on the collected information. Commonly used forms of information used for user authentication are personal identification numbers (PINs), user identifier and password combinations, fingerprint identification information and iris scanning information.

SUMMARY

A method of authenticating a user can include measuring, using a sensor, blood flow of the user and generating sensor data based on the measuring of the blood flow. The method also can include determining, based on the sensor data, at least a first physiological biomarker of the blood flow measured by the sensor and at least a first morphological characteristic of the blood flow measured by the sensor. The method also can include authenticating the user based, at least in part, on the first physiological biomarker and the first morphological characteristic.

A user device includes a processor configured to initiate executable operations. The executable operations can include measuring, using a sensor, blood flow of the user and generating sensor data based on the measuring of the blood flow. The executable operations also can include determining, based on the sensor data, at least a first physiological biomarker of the blood flow measured by the sensor and at least a first morphological characteristic of the blood flow measured by the sensor. The executable operations also can include authenticating the user based, at least in part, on the first physiological biomarker and the first morphological characteristic.

A computer program product includes a computer readable storage medium having program code stored thereon. The program code is executable by a processor to perform executable operations. The executable operations can include measuring, using a sensor, blood flow of the user and generating sensor data based on the measuring of the blood flow. The executable operations also can include determining, based on the sensor data, at least a first physiological biomarker of the blood flow measured by the sensor and at least a first morphological characteristic of the blood flow measured by the sensor. The executable operations also can include authenticating the user based, at least in part, on the first physiological biomarker and the first morphological characteristic.

This Summary section is provided merely to introduce certain concepts and not to identify any key or essential features of the claimed subject matter. Many other features and arrangements of the invention will be apparent from the accompanying drawings and from the following detailed description.

BRIEF DESCRIPTION OF THE DRAWINGS

The accompanying drawings show one or more arrangements; however, the accompanying drawings should not be taken to limit the invention to only the arrangements shown. Various aspects and advantages will become apparent upon review of the following detailed description and upon reference to the drawings.

FIG. 8 is a flow chart illustrating an example of a method of authenticating a user.

DETAILED DESCRIPTION

Figure 1:
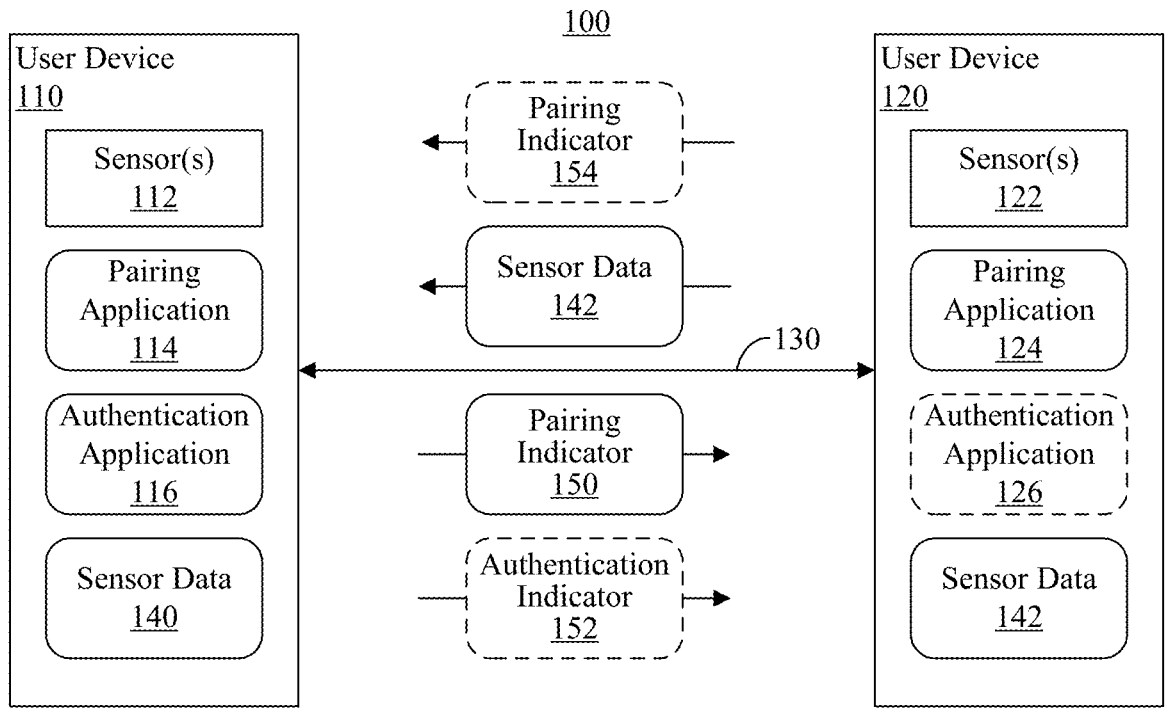
FIG. 1 is a block diagram illustrating an example of a computing environment.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to improving authentication of users. More particularly, the arrangements disclosed herein provide a secure and repeatable manner in which to authenticate users that is superior to previously known methods of authenticating users.

One or more arrangements described within this disclosure are directed to performing authentication of a user based on analyzing the user's blood flow. In accordance with the inventive arrangements disclosed herein, the blood flow of the user can be measured using a sensor, and sensor data can be generated based on measuring the blood flow. One or more physiological biomarkers of the blood flow, one or more morphological characteristics of the blood flow and/or one or more statistical characteristics of the blood flow parameters (hereinafter referred to as "statistical characteristics") can be determined based on the sensor data. The user can be authenticated based on the physiological biomarker(s), the morphological characteristic(s) and/or the statistical characteristic(s).

In this regard, the arterial conduction paths of different users almost never are identical. The present arrangements can generate first parameters representing blood flow through an arterial vessel of a user, compare such parameters to second parameters representing blood flow through an arterial vessel, and determine whether the first parameters match the second parameters. The user can be authenticated based on such determination.

In illustration, a first sensor of a first user device can measure a blood flow and generate first sensor. A second sensor of a second user device can measure a blood flow and generate second sensor data. First parameters representing physiological biomarker(s), morphological characteristic(s) and/or statistical characteristic(s) of blood flow can be determined from the first sensor data, and second parameters representing physiological biomarker(s), morphological characteristic(s) and/or statistical characteristic(s) of blood flow can be determined from the second sensor data. The first parameters can be compared to the second parameters. Responsive to the first parameters matching the second parameters, an indicator indicating the user is authenticated can be output. Otherwise, an indicator indicating the user is not authenticated can be output. The first parameters can be determined to match the second parameters if at least a threshold percentage of the first parameters correlate to the second parameters within a threshold level of correlation.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

FIG. 1 is a block diagram illustrating an example of a computing environment 100. The computing environment can include a user device 110 and a user device 120. Examples of a user device 110, 120 include, but are not limited to, a workstation, a desktop computer, a computer terminal, a mobile computer, a laptop computer, a netbook computer, a tablet computer, a smart phone, a personal digital assistant, a smart watch, a personal fitness tracking device (e.g., fitness tracker), head-mounted display (HMDs), smart glasses, a gaming device, a set-top box, a smart television, a smart refrigerator, a smart security device/system, and so on.

Each of the user devices 110, 120 can include one or more sensors 112, 122. Examples of the sensors 112, 122 include, but are not limited to, heart rate sensors, photoplethysmogram (PPG) sensors (e.g., pulse oximeters), electrocardiography (ECG) sensors, respiratory sensors, galvanic skin response (GSR) sensors and cameras (e.g., video cameras) The sensors 112, 122 can operate using transmittance or reflectance operation modes. Further, each of the user devices 110, 120 can include a respective pairing application 114, 124. The pairing applications 114, 124 can be configured to pair each of the user devices 110, 120 with other user devices, for example to pair the user device 120 with the user device 110. In addition, the user device 110 can include an authentication application 116. The authentication application 116 can be configured to authenticate a user, for example during a process of pairing the user device 110 with another user device (e.g., the user device 120). Optionally, the user device 120 can include an authentication application 126 configured to authenticate a user, but the present arrangements are not limited in this regard.

In operation, a user can initiate a pairing operation to pair the user device 110 with the user device 120. The user can initiate the pairing operation using the pairing application 114 and/or the pairing application 124. During the pairing operation, the user device 110 and/or the user device 120 can establish a communication link 130 between the user devices 110, 120. The communication link 130 can be a wireless communication link or a wired communication link. Examples of a wireless communication link include a personal area network (e.g., Bluetooth®) link, a near filed communication (NFC) link, and an IEEE 802.11 (e.g., WiFi™) link. Examples of a wired communication link include a universal serial bus (USB™) link and an IEEE-1394 link. Still, any other suitable wireless and/or wired communication links can be used, and the present arrangements are not limited in this regard.

During the pairing operation, the sensor 112 can measure biometric parameters of the user and generate corresponding sensor data 140. Similarly, the sensor 122 can measure biometric parameters of the user and generate corresponding sensor data 142. The sensor data 140, 142 can include, for example, data representing characteristics of blood flow through a respective arterial vessel. The arterial vessel can be in a body of the user. For example, the arterial vessel can be in a finger, in a wrist, in an arm, in a leg, in an ankle, in a chest, in a forehead, etc. In this regard, the present arrangements are not limited to any specific location on the body of the user where the blood flow characteristics are measured.

In illustration, the sensor data 140, 142 can include data representing physiological biomarkers (e.g., hear rate, heart rate variability, arterial tone, respiration, oxygen saturation, total peripheral resistance, aging index, ECG, pulse wave transmit time (PWTT), etc.), data representing morphological characteristics of blood flow signals (e.g., shape of blood flow signals, lengths of systolic and diastolic phases, stroke volume of systolic and diastolic phases) and/or statistical characteristics determined from blood flow measurements. Note that ECG and PPG measurements allow establishment of a PWTT wave measurement from one point on the body to another, typically from aorta to the distal point. Addition of ECG to PWTT measurements can make it easy to determine whether a PWTT is consistent for verifying the user's identity or parameters relating to the user's physiology. Various types of sensor data will be described herein in further detail.

The user device 120 can communicate sensor data 142 to the user device 110 (e.g., the pairing application 114) via the communication link 130. The pairing application 114 can communicate the sensor data 142 to the authentication application 116, and initiate the authentication application 116 to compare the sensor data 142 to the sensor data 140 and determine whether the sensor data 142 matches to the sensor data 140. The authentication application 116 can determine that the sensor data 142 matches the sensor data 140 if a level of correlation between the sensor data 140 and the sensor data 142 meets or exceeds a threshold level of correlation. The authentication application 116 can determine that the sensor data 142 does not match to the sensor data 140 if the level of correlation between the sensor data 140 and the sensor data 142 does not meet or exceed the threshold level of correlation.

Responsive to the authentication application 116 determining whether the sensor data 142 matches to the sensor data 140, the authentication application 116 can communicate results of the comparison to the pairing application 114. In response, the pairing application 114 can communicate a pairing indicator 150 to the user device 120 (e.g., the pairing application 124) via the communication link 130. If the sensor data 142 matches the sensor data 140, the paring indicator 150 can indicate that pairing between the user device 110 and the user device 120 is authorized, and the pairing applications 114, 124 can complete the pairing process to pair the user device 110 and the user device 120. If, however, the sensor data 142 does not match the sensor data 140, the paring indicator 150 can indicate that pairing between the user device 110 and the user device 120 is not authorized. Further, the pairing applications 114, 124 can terminate the pairing process. In this regard, the pairing indicator 150 can indicate to the pairing application 124 whether to continue or terminate the pairing process.

In another aspect of the present arrangements, responsive to the authentication application 116 determining whether the sensor data 142 matches to the sensor data 140, the authentication application 116 can communicate results of the comparison to user device 120. For example, the authentication application 116 can communicate results of the comparison to the pairing application 124 as an authentication indicator 152. If the authentication indicator 152 indicates that the sensor data 142 matches the sensor data 140, the pairing application 124 can communicate a pairing indicator 154 to the user device 110 (e.g., the pairing application 114) via the communication link 130, and the pairing applications 114, 124 can complete the pairing process to pair the user device 110 and the user device 120. If, however, the authentication indicator 152 indicates that the sensor data 142 does not match the sensor data 140, the pairing applications 114, 124 can terminate the pairing process. In this regard, the pairing indicator 154 can indicate to the pairing application 114 whether to continue or terminate the pairing process.

In one aspect of the present arrangements, the processes described herein can be implemented to allow a user to make secure digital payments using a mobile device (e.g., a smart phone, a smart watch, smart glasses, etc.). In illustration, systems using the disclosed arrangements can facilitate processes for secure peer-to-peer payment for facilities without merchants or no infrastructure which supports smartphone payments. Merchants in rural areas or shopkeepers at bazaars may not necessarily have machines to accept payments by credit card or using certain modes of payments. The merchants or shopkeepers, however, may have mobile devices and the present arrangements can be implemented enable exchanges between them and prospective consumers.

In one aspect of the present arrangements, the processes described above can be implemented along with one or more other forms of authentication in order to authenticate the user. For example, the above described processes can be performed to authenticate the user in addition to authentication processes using a personal identification number (PIN), password, fingerprint, iris scan, vein scan, arterial stiffness, eye color, user weight, user height, user inputs, queries, results from additional sensor parameters, and/or a combination of such authentication processes. The combination of the above described processes with one or more other forms of authentication can provide a robust authentication and that provides very strong security.

In another aspect of the present arrangements, authentication of the user in accordance with the above described processes can be used to validate live usage of devices, for example consumer electronic devices connected in the Internet of Things (IoT) domain. For instance, the user can be authenticated in accordance with the authentication aspects of the above described processes in order to authorize the user to control a user device, such as the user device 110 and/or user device 120, regardless of whether the user devices 110, 120 are being paired. By way of example, assume the user device 110 is a media device (e.g., a smart television, a HMD, etc.), and the user is attempting to use the user device 110. The user can be authenticated as described.

Based on the user successfully being authenticated, the user can be allowed to use the user device 110 and/or user certain aspects of the user device 110, for example to control presentation of content, control media playback, control parental lock states, configure the user device 110, provide access to one or more user manipulated controls, etc. Further, based on authenticating the user, the user device 110 can customize configuration of the user device 110 and/or presentation of content for the user, perform a customized search for content for the user, etc. In another example, assume the user device 110 is a smart refrigerator. The user can be authenticated in accordance with the authentication aspects of the above described processes in order to authorize the user to change settings in the smart refrigerator and/or present content via the smart refrigerator. In another example, assume the user device 110 is a security system/device. The user can be authenticated in accordance with the authentication aspects of the above described processes in order to authorize the user to access an entrance and/or open a safe.

In another aspect of the present arrangements, authentication of the user in accordance with the above described processes can be used to perform authentication using remote oximetry sensing, for example via a camera. In illustration, image data captured by a security camera at an entrance to a secured area can be used to perform remote oximetry sensing of a user. The user can be authenticated by comparing results of the remote oximetry sensing with results of PPG sensing performed on the user by a smartphone, smart watch, smart glasses or other device. This can enable fast, yet secure, authentication of the user when the user is attempting to enter the secured area.

In another example, image data captured by a camera within a vehicle can be used to perform remote oximetry sensing of a user and/or one or more ECG sensors with the vehicle (e.g., attached to a steering wheel) can be used to perform oximetry sensing of a user. Again, the user can be authenticated by comparing results of the oximetry or remote oximetry sensing with results of PPG sensing performed on the user by a smartphone or other device. The vehicle (e.g., a device or system of/within the vehicle) can provide certain features to the user based on determining an identity of the user based on the authentication, and based on whether the user is a driver or passenger. For instance, the device or system of/within the vehicle can provide personalized mirror/seat adjustment, smart phone functions, etc.

Further, the user can receive relevant feedback (e.g., navigation guidance via the user's smart phone, smart watch, smart glasses, etc.).

In another example, systems using the disclosed processes described herein can provide a process for registering and encrypting intents for (lightweight) data transfer without mass storage or mail across multiple devices. The data transfer can enable users to either receive data (e.g., pictures and media at theme parks, museums, entrances, or fitness data) or provide data (e.g., transit tickets or tickets for prizes or games). For example, a user may be on some attraction at a touristic site where they can take his/or photograph(s) with a camera containing communications technology that makes it capable of transmitting files as well. A user can request to transfer the photograph(s) captured on the camera system and simultaneously launch an intent to retrieve the data on their user device (e.g., smartphone), and the process can be enabled in a verified manner using the authentication techniques described herein.

In another aspect of the present arrangements, the sensor data 140 generated by the user device 110 and/or the sensor data 142 generated by the user device 120 can be communicated to a remote system (not shown) and used for remote healthcare assessments. Further, the authentication processes described above can be used by the remote system to authenticate access of the user to healthcare records and/or subscriptions provided by the remote system using the user device 110 and/or user device 120. The remote system can implement the user authentication processes described above in order to validate the user based on the sensor data 140 and/or the sensor data 142. Such an arrangement can reduce burdens in terms of need for local availability of medical resources. Instead, the present arrangement can enable secure remote access to the medical resources.

In another example, the present arrangements can be implemented to enhance an experience of retrieving fitness data from equipment or devices integrating ECG sensors, such as exercise equipment and smart weighing scales. In illustration, a user monitoring his/her training performance commonly may use exercise equipment having integrated ECG sensors and providing capabilities for tracking various physical metrics. The user can initiate processes described herein to authenticate the user with the exercise equipment. For example, the user device 110 can be component of a particular exercise equipment, or a device/system communicatively linked to a plurality of exercise equipment. The user device 110 can be configured to, based on successful authentication of the user via the user device 120 (e.g., smart phone, smart watch, smart glasses, etc.) communicate various data (e.g., exercise data, parameters monitored during exercise, etc.) collected by the exercise equipment for the user to the user device 120. The user device 120 can analyze the data for the purposes of developing improved training regiments and/or present the data to the user. In this regard, the user device 120 can validate wellness product related parameters.

It should be noted that cardiovascular disease (CVD) is more prevalent in users who are middle aged or older, and cardiac arrhythmia may onset at any time. Thus, blood flow may characteristics of a user may change over time. The present arrangements, however, can rely on currently obtained blood flow characteristics, not on a comparison to historical blood flow characteristics. Accordingly, cardiac arrhythmia or onset of CVD related to ECG abnormalities in a user will not adversely affect the user authentication processes described herein. Moreover, since the present arrangements can rely on currently obtained blood flow characteristics, not on a comparison to historical blood flow characteristics, user afflictions such as burns, skin issues, etc. need not affect the user authentication processes described herein.

Figure 2:
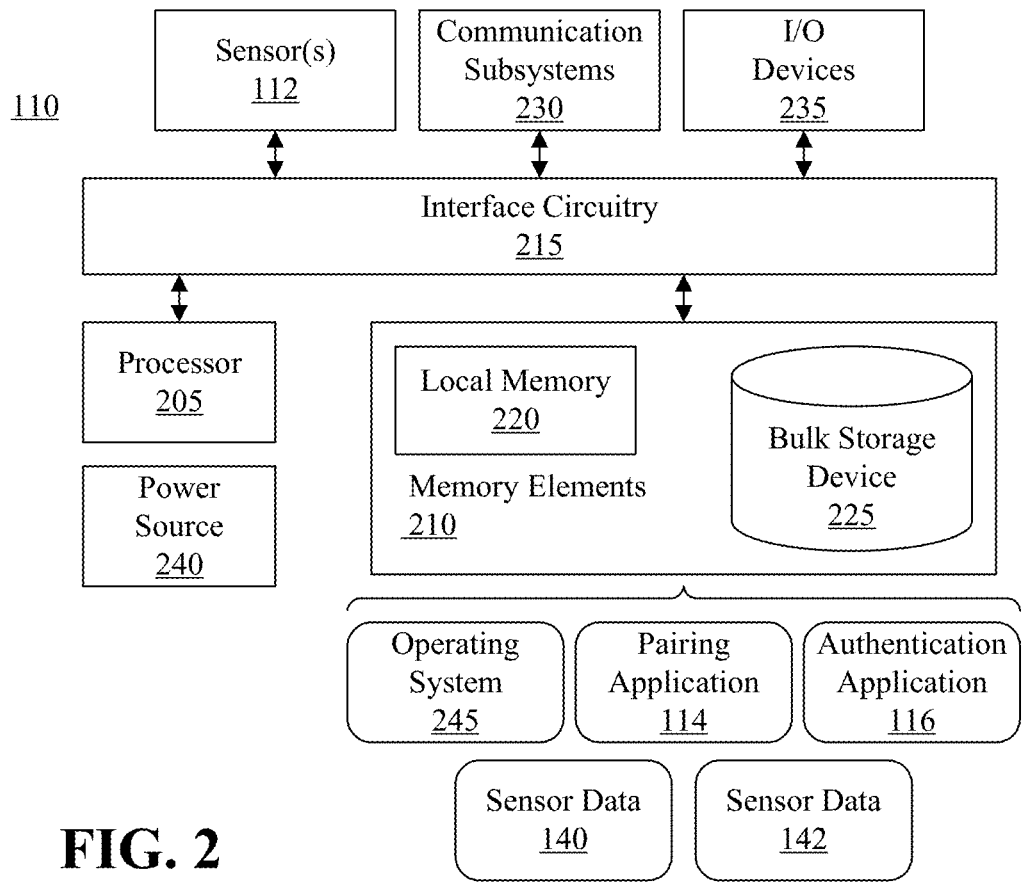
FIG. 2 is a block diagram illustrating example architecture for a user device.

FIG. 2 is a block diagram illustrating example architecture for the user device 110. The user device 120 can be configured in a similar manner.

The user device 110 can include at least one processor 205 (e.g., a central processing unit, an image processor, a digital signal processor, a data processor, etc.) coupled to memory elements 210 via interface circuitry 215 (e.g., a system bus or other suitable circuitry). As such, the user device 110 can store program code within the memory elements 210. The processor 205 can execute the program code accessed from the memory elements 210 via the interface circuitry 215. In one aspect, the processor 205, memory elements 210, and/or interface circuitry 215 can be implemented as separate components. In another aspect, the processor 205, memory elements 210, and/or interface circuitry 215 can be integrated in one or more integrated circuits. The various components in user device 115, for example, can be coupled by one or more communication buses or signal lines (e.g., interconnects and/or wires). In one aspect, the memory elements 210 may be coupled to interface circuitry 215 via a memory interface (not shown).

The memory elements 210 can include one or more physical memory devices such as, for example, local memory 220 and one or more bulk storage devices 225. Local memory 220 refers to random access memory (RAM) (e.g., volatile memory) or other non-persistent memory device(s) generally used during actual execution of the program code. The bulk storage device(s) 225 can be implemented as a hard disk drive (HDD), solid state drive (SSD), or other persistent data storage device. The user device 110 also can include one or more cache memories (not shown) that provide temporary storage of at least some program code in order to reduce the number of times program code must be retrieved from the bulk storage device 225 during execution.

The sensors 112 can be coupled to the interface circuitry 215 to facilitate the functions and/or operations described within this disclosure including the generation of sensor data. The sensors 112 may be coupled to the interface circuitry 215 directly or through one or more intervening I/O controllers (not shown).

Communication functions can be facilitated through one or more communication subsystems 230. The communication subsystems 230 can include, but are not limited to, radio frequency receivers and transmitters, optical (e.g., infrared) receivers and transmitters, network adapters, communication busses (e.g., serial busses), and so forth. The specific design and implementation of the communication subsystems 230 can depend on the particular type of user device 115 implemented and/or the communication network(s) over which the user device 115 is intended to operate. For purposes of illustration, the communication subsystem(s) 230 may be designed to operate over one or more mobile networks (e.g., GSM, GPRS, EDGE), a WiFi network which may include a WiMax network, a personal area network, near field communication, direct wired communication links and/or any combination of the foregoing.

I/O devices 235 can be coupled to interface circuitry 215. Examples of I/O devices 235 can include, but are not limited to, display devices, touch sensitive display devices, track pads, keyboards, pointing devices, buttons or other physical controls, and so forth. A touch sensitive device such as a display screen and/or a pad is configured to detect contact, movement, breaks in contact, etc., using any of a variety of touch sensitivity technologies. Example touch sensitive technologies include, but are not limited to, capacitive, resistive, infrared, and surface acoustic wave technologies, other proximity sensor arrays or other elements for determining one or more points of contact with a touch sensitive device, etc. One or more of I/O devices 235 may be adapted to control functions of the sensors 112, subsystems, etc.

The user device 110 further includes a power source 240. The power source 240 is capable of providing electrical power to the various elements of the user device 110. In one arrangement, the power source 240 can be implemented as one or more batteries. The batteries may be implemented using any of a variety of different battery technologies whether disposable (e.g., replaceable) or rechargeable. In another arrangement, the power source 240 can be configured to obtain electrical power from an external source and provide power (e.g., DC power) to the elements of the user device 110. In the case of a rechargeable battery, the power source 240 further may include circuitry that is capable of charging the battery or batteries when coupled to an external power source.

The memory elements 210 can store software components of the user device 110, for example an operating system 245, the pairing application 114 and the authentication application 116. The operating system 245 may include instructions for handling system services and for performing hardware dependent tasks. Examples of the operating system 245 include, but are not limited to, LINUX, UNIX, a mobile operating system, an embedded operating system, etc.

The memory elements 210 also may store, at least temporarily, the sensor data 140, as well as sensor data 142 received from the user device 120.

In one arrangement, using the processor 205, the pairing application 114 and/or authentication application 116 can store the sensor data 140, 142 temporarily in the memory elements 210 (e.g., in the local memory 220) while being processed by the pairing application 114 and/or authentication application 116, for example as streaming user data. The pairing application 114 and/or authentication application 116 can delete the sensor data 140, 142 in response to such processing being completed. In this regard, the authentication processes described herein can be performed exclusively on streaming sensor data 140, 142. Thus, the risk of the sensor data 140, 142 being substituted with sensor data from a stored file can be mitigated. In this regard, the pairing application 114 and the pairing application 124 (FIG. 1) can be configured to only generate as the sensor data 140, 142 sensor data presently being generated by the sensors 112, 122, and not sensor data previously stored, and the authentication application 116 can process the sensor data 140, 142 in real time as the authentication application 116 receives the sensor data 140, 142.

Nonetheless, the present arrangements are not limited in this regard. For example, the pairing application 114 and/or authentication application 116 can persist the sensor data 140, 142 to the bulk storage device 225 as the sensor data 140, 142 is streamed, though additional security measures can be implemented to ensure the sensor data 140, 142 is not compromised.

The memory elements 210 may also store other program code (not shown). Examples of other program code may include instructions that facilitate communicating with one or more additional devices, one or more computers and/or one or more servers; graphic user interface processing; sensor-related processing and functions; phone-related processes and functions; electronic-messaging related processes and functions; Web browsing-related processes and functions; media processing-related processes and functions; GPS and navigation-related processes and functions; security functions; camera-related processes and functions including Web camera and/or Web video functions; and so forth. The memory elements 210 also may store one or more other application(s) (not shown).

The various types of instructions and/or program code described are provided for purposes of illustration and not limitation. The program code may be implemented as separate software programs, procedures, or modules. The memory elements 210 can include additional instructions or fewer instructions. Furthermore, various functions of user device 110 may be implemented in hardware and/or in software, including in one or more signal processing and/or application specific integrated circuits.

Program code stored within the memory elements and any data items used, generated, and/or operated upon by user device 110 are functional data structures that impart functionality when employed as part of the device. Further examples of functional data structures include, but are not limited to, sensor data, data obtained via user input, data obtained via querying external data sources, baseline information, and so forth. The term "data structure" refers to a physical implementation of a data model's organization of data within a physical memory. As such, a data structure is formed of specific electrical or magnetic structural elements in a memory. A data structure imposes physical organization on the data stored in the memory as used by a processor.

In one or more arrangements, one or more of the various sensors 112 and/or subsystems described with reference to user device 110 may be separate devices that are coupled or communicatively linked to user device 110 through wired or wireless connections. One or more of the sensors 112 may be worn directly by the user and provide data to user device 110 via a wired or wireless connection. The user device 110 also may include additional sensors. Examples of such additional sensors include, but are not limited to gyroscopes, global positioning system (GPS) receivers, etc.

The user device 110 may include fewer components than shown or additional components not illustrated in FIG. 2 depending upon the particular type of system that is implemented. In addition, the particular operating system and/or application(s) and/or other program code included may also vary according to system type. Further, one or more of the illustrative components may be incorporated into, or otherwise form a portion of, another component. For example, a processor may include at least some memory.

The user device 110 is provided for purposes of illustration and not limitation. A device and/or system configured to perform the operations described herein may have a different architecture than illustrated in FIG. 2. The architecture may be a simplified version of the architecture described in connection with the user device 110 and include a processor and memory storing instructions. The architecture may include one or more sensors as described herein. The user device 110, or a system similar to user device 110, is capable of collecting data using the various sensors of the device or sensors coupled thereto. It should be appreciated, however, that the user device 110 may include fewer sensors or additional sensors. Within this disclosure, data generated by a sensor is called "sensor data."

Figure 3:
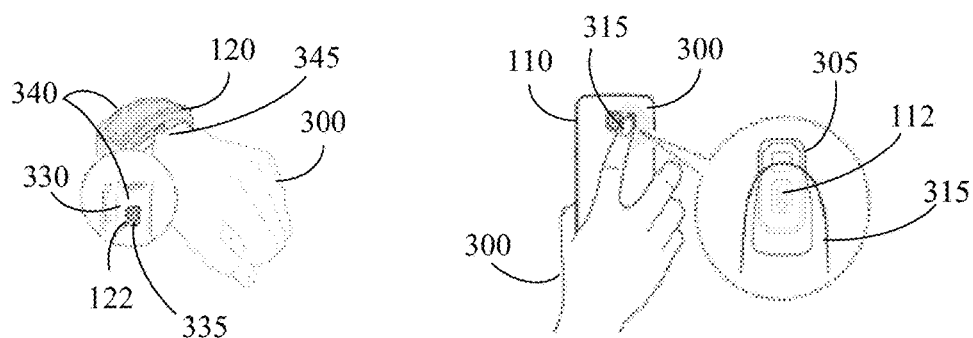
FIG. 3 depicts an example of user devices being used to implement authentication.

FIG. 3 depicts an example of user devices 110, 120 being used to implement authentication. In this example, the user device 110 can be a smart phone, the user device 120 can be a smart watch or personal fitness tracking device, and the sensors 112, 122 can be heart rate sensors or PPG sensors integrated in the respective user devices 110, 120. The respective user devices 110, 120 can activate the sensors to collect the biometric parameters of a user 300, for example during authentication of the user 300, as previously described.

The sensor 112 can be disposed in/on the user device 110 in a location easily accessible for use by a user 300, for example behind a window 305 on a shell 310 (e.g., case) of the user device 110. To facilitate measurement of the biometric parameters of the user 300, the user 300 can position an appendage 315 (e.g., a finger) of the user 300 proximate to the sensor 112, for example within a threshold distance of the sensor 112. In illustration, the user can touch the window 305, behind which the sensor 112 is located, with the appendage 315. The user 300 can do so while holding the user device 110, or while the user device 110 is laying on a surface with the sensor 112 facing upward to allow the user to place the appendage 315 proximate to the sensor 112.

The sensor 222 can be disposed in/on the user device 120 in a location proximate to skin/flesh of the user 300. For example, the sensor 222 can be disposed in/on a back 330 of the user device 120. In illustration, the sensor 222 can be disposed behind a window 335 on the back 330 of a shell 340 (e.g., case) of the user device 120. When the user device 120 is worn by the user, for example on the user's wrist 345, the sensor can be positioned proximate to the skin/flesh of the wrist 345.

In this example, the user 300 can wear the user device 120 on the wrist 345 of a first arm, and the user 300 can touch the window 305 of the 110 with an appendage 315 of the other arm. Accordingly, each of the sensors 112, 122 can simultaneously detect the biometric parameters of the user 300 and generate respective sensor data 140, 142 used during the authentication process to pair the user devices 110, 120.

Figure 4:
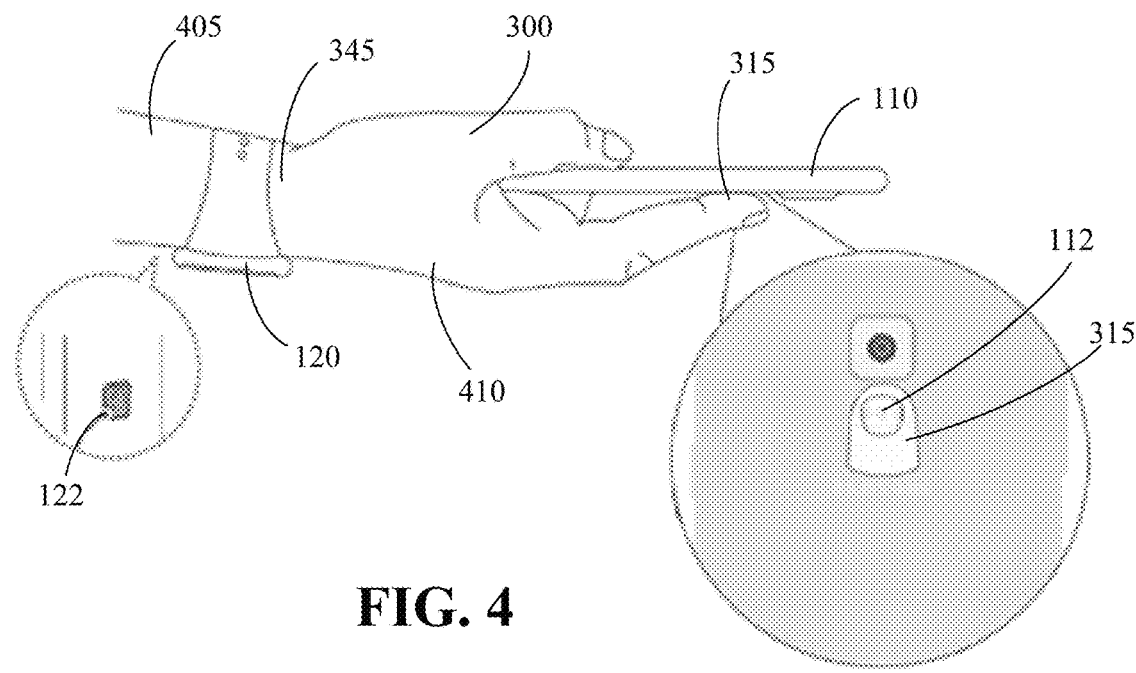
FIG. 4 depicts another example of user devices being used to implement authentication.

FIG. 4 depicts another example of user devices 110, 120 being used to implement authentication. The arrangement depicted in FIG. 4 is similar to that depicted in FIG. 3, except that the appendage 315 and the wrist 345 can be of the same arm 405 of the user 300. For example, the appendage 315 can be connected to a hand 410, which is connected to the wrist 345, which is connected to the arm 405.

Figure 5:
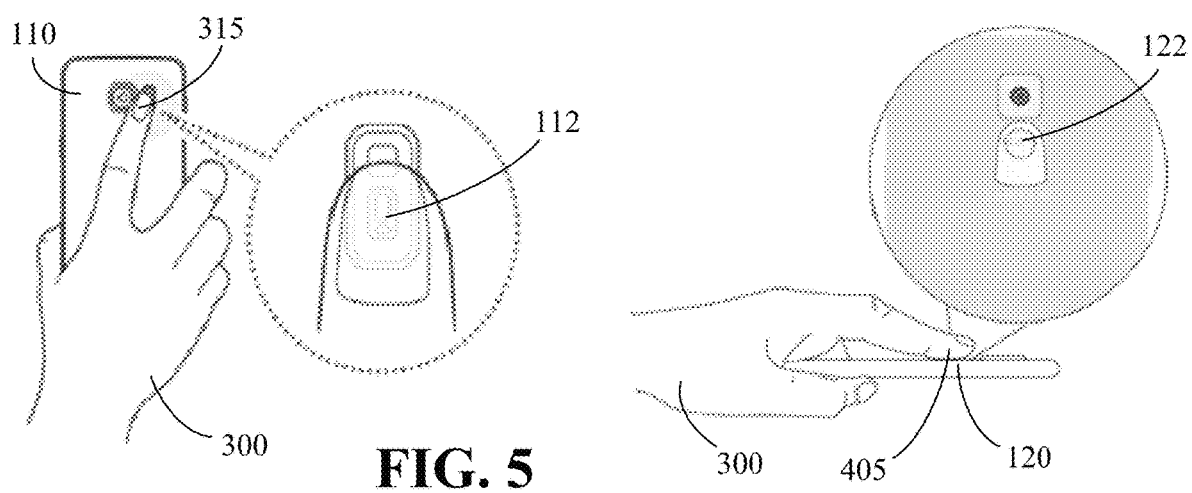
FIG. 5 depicts another example of user devices being used to implement authentication.

FIG. 5 depicts another example of user devices 110, 120 being used to implement authentication. The arrangement depicted in FIG. 5 is similar to that depicted in FIG. 3, except that the user device 120 also can be a smart phone. The sensor 122 can be in/on the user device 120 in a location easily accessible for use by a user 300, for example as described in FIG. 3 with respect to the sensor 112 and the user device 110. Thus, the user can pair the user devices 110, 120 by holding the user device 110 in one hand and holding the user device 120 in another hand. Of course, the user can lay one or both of the user devices 110, 120 on a surface with the sensor(s) 112, 122 facing upward to allow the user to place the respective appendages proximate to the sensors 112, 122.

Figure 6:
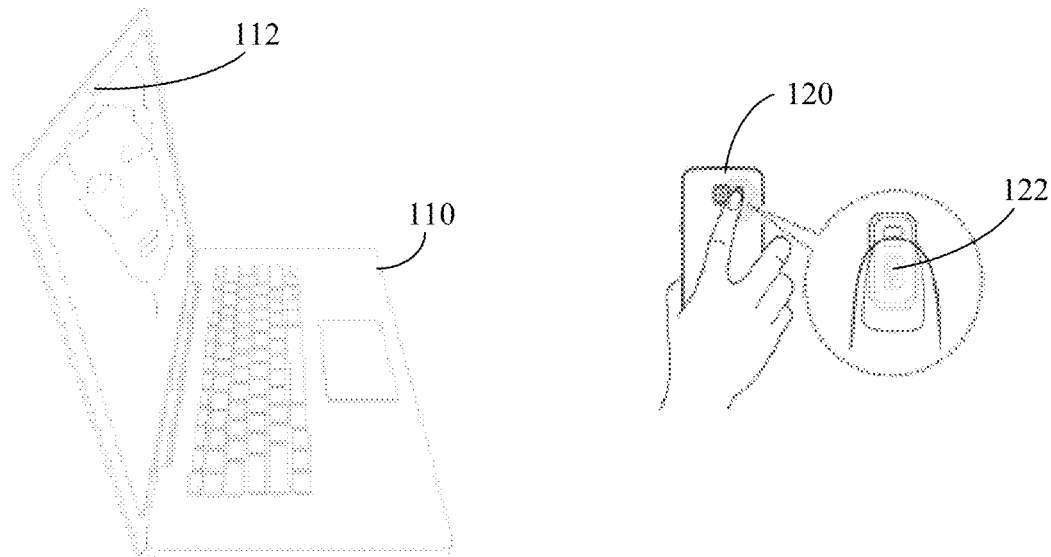
FIG. 6 depicts another example of user devices being used to implement authentication.

FIG. 6 depicts another example of user devices 110, 120 being used to implement authentication. In this example, the user device 110 can be a computer and the user device 120 can be a smart phone. Further, the sensors 112, 122 can be heart rate sensors or PPG sensors. In another arrangement, the sensor 112 can be a camera, and the sensor 122 can be a heart rate sensor or PPG sensor.

Images captured by the camera can be processed by the user device 110, for example by the authentication application 116 or another application executing on the user device 110, to generate the sensor data 140 (FIG. 1). In illustration, the authentication application 116 (or other application) can process image data generated by the camera to identify biometric features and generate sensor data corresponding to the biometric features. For instance, the image data for a sequence of images can indicate movement by a user's skin/flesh due to the user's heart beat or changes in light absorption by the user's skin/flesh. The authentication application 116 (or other application) can process the sequence of images to generate a plethysmogram, and include the plethysmogram in the sensor data 140. In the case that the plethysmogram is measured by changes in light absorption by the user's skin/flesh, the plethysmogram can be a photoplethysmogram (PPG).

The sensor data 142 (FIG. 1) generated by the sensor 122 also can include a plethysmogram (e.g., a PPG). Thus, even though the sensors 112, 122 may be different types of sensors, the respective sensor data 140, 142 generated by the respective sensors 112, 122 can be compared, as previously described, to determine whether the sensor data 142 matches the sensor data 140.

Figure 7:
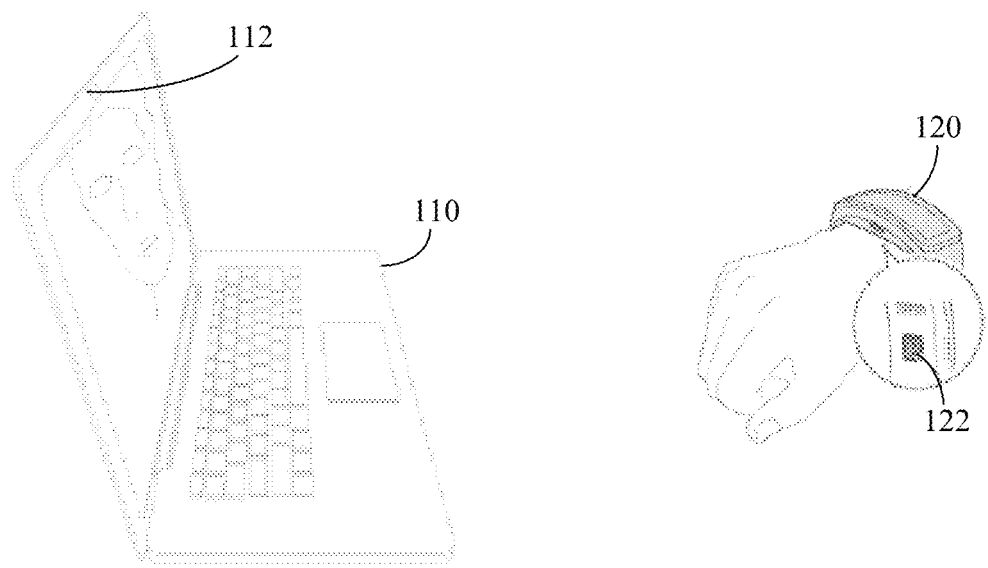
FIG. 7 depicts another example of user devices being used to implement authentication.

FIG. 7 depicts another example of user devices 110, 120 being used to implement authentication. The arrangement depicted in FIG. 7 is similar to that depicted in FIG. 6, except that in the example presented in FIG. 7 the user device 120 can be a smart watch or personal fitness tracking device including a sensor 122.

FIG. 8 is a flow chart illustrating an example of a method 800 of authenticating a user. At step 805, a first sensor (e.g., the sensor 112) can measure blood flow of a user and generate first sensor data 140 based on the measuring of the blood flow. At step 810, the authentication application 116 can determine, based on the first sensor data 140, at least a first physiological biomarker of the blood flow measured by the first sensor 112 and at least a first morphological characteristic of the blood flow measured by the first sensor 112, and generate corresponding parameters. In one non-limiting arrangement, the authentication application 116 also can determine, based on the first sensor data 140, at least a first statistical characteristic of the blood flow measured by the first sensor 112, and generate at least one corresponding parameter. The authentication application 116 can determine the first physiological biomarker(s), the first morphological characteristic(s) and, optionally, the first statistical characteristic(s) by processing the sensor data 140, as will be described herein in further detail.

At step 815, the authentication application 116 can receive second sensor data 142 generated by a second sensor (e.g., the sensor 122). The second sensor data 142 can be received, in real time, simultaneously with the first sensor data being measured at step 805 and the corresponding parameters being generated at step 810.

Optionally, at step 820, the authentication application 116 can determine, based on the second sensor data 142, at least a second physiological biomarker of a blood flow measured by the second sensor 122 and at least a second morphological characteristic of the blood flow measured by the second sensor 122, and generate corresponding parameters. The authentication application 116 also can determine, based on sensor data 142, at least a second statistical characteristic of the blood flow measured by the second sensor 122, and generate at least one corresponding parameter. In another aspect of the present arrangements, rather than the authentication application 116 generating the parameters from the second sensor data 142, the authentication application 126 can generate the parameters corresponding to second physiological biomarker(s), the second morphological characteristic(s) and, optionally, the second statistical characteristic(s). In such arrangement, the sensor data 142 can include those parameters.

At step 825, the authentication application 116 can compare at least the first physiological biomarker to at least the second physiological biomarker and compare at least the first morphological characteristic to at least the second morphological characteristic. In one non-limiting arrangement, the authentication application 116 also can compare the at least the first statistical characteristic to at least the second statistical characteristic.

At step 830, the authentication application 116 can determine whether at least the first physiological biomarker matches at least the second physiological biomarker and determine whether at least the first morphological characteristic matches at least the second morphological characteristic. In one non-limiting arrangement, the authentication application 116 also can determine whether at least the first statistical characteristic matches at least the second statistical characteristic. In this regard, the authentication application 116 can perform equivalence checks to determine whether the first physiological biomarker is equivalent to at least the second physiological biomarker, determine whether the first morphological characteristic is equivalent to at least the second morphological characteristic, and determine whether the first statistical characteristic is equivalent to at least the second statistical characteristic. The equivalency checks can incorporate any of a variety of approaches including logic, graphical analysis, search methods, heuristics, and machine learning techniques such as, for example, support vector machine (SVM) classification. The machine learning techniques can be implemented, for example, using neural networks accessed by the authentication application 116.

Referring to decision box 835, the authentication application 116 can, responsive to determining that at least the first physiological biomarker matches at least the second physiological biomarker and determining that at least the first morphological characteristic matches at least the second morphological characteristic, proceed to step 840. At step 840, the authentication application 116 can output an indicator indicating the user is authenticated. For example, the authentication application 116 can output the indicator to the pairing application 114 and/or the pairing application 124. In one non-limiting arrangement, the authentication further can be based on determining that at least the first statistical characteristic matches at least the second statistical characteristic.

Referring again to decision box 835, the authentication application 116 can, responsive to determining that at least the first physiological biomarker does not match at least the second physiological biomarker and/or determining that at least the first morphological characteristic does not match at least the second morphological characteristic, proceed to step 845. At step 845, the authentication application 116 can output an indicator indicating the user is not authenticated. For example, the authentication application 116 can output the indicator to the pairing application 114 and/or the pairing application 124. The authentication further can be based on determining that at least the first statistical characteristic does not match at least the second statistical characteristic.

In another aspect of the present arrangements, steps 810-835 can be iteratively performed on various parameters using a segmented analysis of the physiological biomarkers, the morphological characteristics and, optionally, the statistical characteristics. In illustration, steps 810-835 initially can be performed exclusively on the physiological biomarkers. Responsive to determining that the physiological biomarker(s) do not match at step 830 and decision box 835, the process can proceed to step 845. Responsive to determining that the physiological biomarker(s) do match, the process can return to step 810, and steps 810-835 can be performed exclusively on the morphological characteristic(s). Responsive to determining that the morphological characteristic(s) do not match at step 830 and decision box 835, the process can proceed to step 845. Responsive to determining that the morphological characteristic(s) do match, the process can return to step 810, and steps 810-835 can be performed exclusively on the statistical characteristic(s). Responsive to determining that the statistical characteristic(s) do match at step 830 and decision box 835, the process can proceed to step 840. Responsive to determining that the statistical characteristic(s) do not match at step 830 and decision box 835, the process can proceed to step 845.

In one aspect of the present arrangements, in addition to step 830, one or more other forms of authentication processes can be used to determine whether other types of parameters match. Such parameters can include, for example, parameters corresponding to PINs, passwords, fingerprints, iris scans, vein scans and/or a combination of such parameters. In such an arrangement, a determination can be made as to whether the other parameter(s) match. The indicators output at steps 840 and 845 can be based on such determination(s). For example, step 840 can be performed responsive to determining that at least the first physiological biomarker matches at least the second physiological biomarker, determining that at least the first morphological characteristic matches at least the second morphological characteristic and/or determining that at least the first statistical characteristic matches at least the second statistical characteristic, in addition to determining the other parameter(s) match. Step 845 can be performed responsive to determining that at least the first physiological biomarker does not match at least the second physiological biomarker, determining that at least the first morphological characteristic does not match at least the second morphological characteristic, determining that at least the first statistical characteristic does not match at least the second statistical characteristic, and/or determining one or more of the other parameter(s) do not match.

Figure 9:
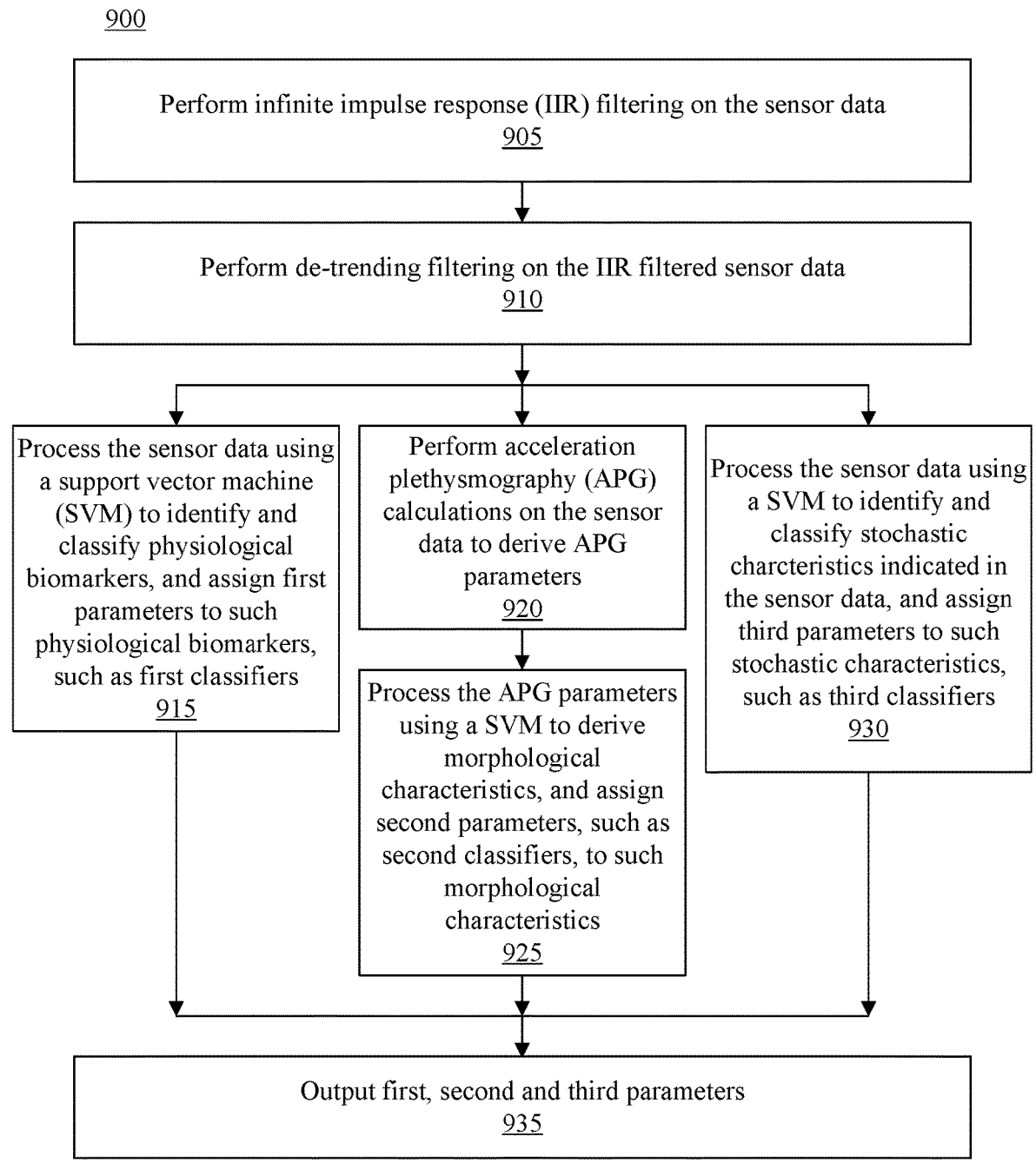
FIG. 9 is a flow chart illustrating an example of a method of processing sensor data to generate parameters used for authenticating a user.

FIG. 9 is a flow chart illustrating an example of a method 900 of processing sensor data 140, 142 to generate parameters used for authenticating a user. The method 900 can be implemented to determine the various parameters in steps 810 and 820 of FIG. 8, and used for the comparison of the characteristics performed in step 825 of FIG. 8. The method 900 can be performed for each of the sensor data 140 and the sensor data 142. The method can be performed by the authentication application 116 (FIG. 1) for both the sensor data 140 and the sensor data 142, or performed by the authentication application 116 for the sensor data 140 and performed by the authentication application 126 (FIG. 1) for the sensor data 142. In the following example steps, reference is made to the authentication application 116 performing the various steps on the sensor data 140, but it will be understood that the authentication application 116 and/or authentication application 126 can perform the various steps on the sensor data 142.

At step 905, the authentication application 116 can perform infinite impulse response (IIR) filtering on the sensor data 140. The IIR filtering can include using low pass filtering to remove noise from the sensor data 140, as is known in the art. At step 910, the authentication application 116 can perform de-trending filtering on the IIR filtered sensor data 140. The de-trending filtering can remove a trend from the sensor data 140 that may cause distortion in the sensor data 140, as is known in the art. The de-trending filtering, for example, can perform a polynomial fit to the sensor data 140. Based on the polynomial fit, the de-trending filtering can filter distortion signals.

At step 915, the authentication application 116 can process the sensor data 140 (e.g., the IIR filtered and de-trended sensor data) using a SVM to identify and classify physiological biomarkers (e.g., cardiopulmonary features) indicated in the sensor data 140, and assign first parameters to such physiological features, such as first classifiers.

At step 920, the authentication application 116 can perform acceleration plethysmography (APG) calculations on the sensor data 140 (e.g., the IIR filtered and de-trended sensor data) to derive APG parameters. For example, the authentication application 116 can perform APG calculations on PPG data contained in the sensor data 140. At step 925, the authentication application 116 can process the APG parameters using a SVM to derive morphological characteristics from the APG parameters, and assign second parameters, such as second classifiers, to such morphological characteristics.

At step 930, the authentication application 116 can process the sensor data 140 (e.g., the IIR filtered and de-trended sensor data) using a SVM to identify and classify statistical characteristics (e.g., higher-order statistics) indicated in the sensor data 140, and assign third parameters to such statistical characteristics, such as third classifiers.

Steps 920 and 935 can be implemented sequentially, while steps 915 and 930 can be implemented in parallel with performance of steps 925, 930.

At step 935, the first, second and third parameters can be output for use in the comparison performed at step 825 of FIG. 8. In this regard, the first parameters can represent physiological biomarkers of the blood flow, the second parameters can represent morphological characteristics of the blood flow, and the third parameters can represent statistical characteristics of the blood flow.

Figure 10:
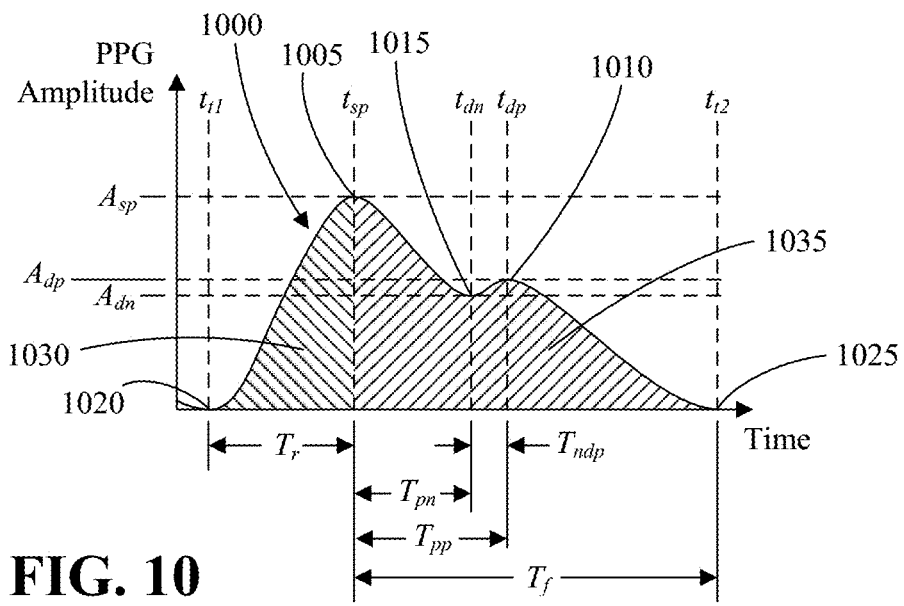
FIG. 10 depicts an example of a blood flow waveform.

FIG. 10 depicts an example of a blood flow waveform 1000. The waveform 1000 can be one in a series of blood flow waveforms be detected using a sensor, for example the sensor 112, and represented in the sensor data 140. The sensor data 142 can include data representing similar waveforms. The authentication application 116 can process the data representing the waveform 1000 to generate the parameters for the physiological biomarkers, morphological characteristics and statistical characteristics of the blood flow. In this regard, practically multithreaded processing can be used to determine such features. A number of features may be determined using information about extrema in a detrended PPG signal so that sign changes in a derivative of the detrended PPG signal are used in order to detect extrema in one of the processing threads. The times of extrema as well as corresponding amplitudes of the detrended PPG wave signal can be sub-resolved through quadratic interpolation, and values can be shared among the different threads to compute the various features in real time.

The physiological biomarkers can be extracted between timing of corresponding extrema. It is for these purposes that the number of peaks and troughs can be counted and used to track the number of extrema in the signals. The absolute value of differences between timings of successive peaks can be computed. Standard deviations of tracked timing differences also can be determined. The time periods between ordered trough and peak timings can be used to compute time periods associated with pulse rise and fall times respectively. Trapezoidal numerical integration can be performed using detrended amplitudes of the PPG signal values occurring between successive peak-trough times and trough-peak times in order to obtain values of area under the curve.

Higher-order statistics (HOS) from signals also can be determined for comparing different blood flow signals. Standard formulations such as those known in the art can be used for obtaining HOS. The median as well as means of the detrended PPG amplitudes can be computed and tracked as are root mean squared (RMS) values, kurtosis values, skewness values.

In illustration, the authentication application 116 can identify for the waveform 1000 an amplitude ($A_{sp}$) of a systolic peak 1005, an amplitude ($A_{dp}$) of a diastolic peak 1010, and an amplitude ($A_{dn}$) of a dicrotic notch 1015. The authentication application 116 can generate parameters indicating the respective amplitudes. In addition, the authentication application 116 can identify differences between the amplitudes ($A_{sp}$), ($A_{dp}$) and ($A_{dn}$), and generate parameters indicating the respective amplitude differences. For example, the authentication application 116 can generate a parameter representing the difference between the amplitude ($A_{sp}$) of the systolic peak 1005 and the amplitude ($A_{dp}$) of the diastolic peak 1010, a parameter representing the difference between the amplitude ($A_{sp}$) of the systolic peak 1005 and the amplitude ($A_{dn}$) of the dicrotic notch 1015, and a parameter representing the difference between the amplitude ($A_{dp}$) of the diastolic peak 1010 and the amplitude ($A_{dn}$) of the dicrotic notch 1015.

The parameters indicating the respective amplitudes ($A_{sp}$), ($A_{dp}$) and ($A_{dn}$), troughs ($t_{t1}$), ($t_{t2}$) and various differences can be classified as morphological characteristics, while timing between successive waveforms in a series of waveforms, including the waveform 1000, can be classified as physiological biomarkers. For example, from a series of waveforms, the authentication application 116 can identify amplitudes and troughs of each of the waveforms and, based on the identified amplitudes/troughs, determine a heart rate, heart rate variability, arterial tone, etc. as physiological biomarkers. An absolute difference ($d_a$) in times ($t_{sp}$) of the systolic peak 1005 in successive waveforms, which is indicative of heart rate variability, can be determined by the authentication application 116 using the following equation:

$$d_a = \mathrm{abs}(t_{sp}[i, ppg1] - t_{sp}[i, ppg2])$$

The authentication application 116 also can determine square roots of mean squared differences in times of successive peak times ($t_{sp}$) (RMSSD) of the systolic peak 1005, which can be used to capture rhythm variation, indicate stress, etc.

Further, the authentication application 116 can determine a of rise time ($T_r$) period, of the systolic phase between a time ($t_{t1}$) of a first trough 1020 and a time ($t_{sp}$) of the systolic peak 1005, a fall time ($T_f$) period of the diastolic phase between the time ($t_{sp}$) of the systolic peak 1005 and a time ($t_{t2}$) of a second trough 1025, a pulse propagation time ($T_{pp}$) period between the time ($t_{sp}$) of the systolic peak 1005 and a time ($t_{dp}$) of the diastolic peak 1010, a time ($T_{pn}$) period between the time ($t_{sp}$) of the systolic peak 1005 and a time ($t_{dn}$) of the dicrotic notch 1015, and a time ($T_{ndp}$) period between the time ($t_{dn}$) of the dicrotic notch 1015 and the time ($t_{dp}$) of the diastolic peak 1010. The authentication application 116 can generate parameters indicating the respective time periods and classify those parameters as morphological characteristics. The authentication application 116 can determine various times based on a series of waveforms including the waveform 1000, for example to generate average values as physiological biomarkers of the blood flow. By way of example, the authentication application 116 can determine the fall time ($T_f$) of the diastolic phase using the following equation:

$$T_f = \text{abs}(t_{t2}[i, ppg1] - t_{sp}[i, ppg1])$$

where ppg1 is data contained in the sensor data 140, i is the number of sensed (systolic and diastolic) phases to which a parameter pertains, and [I] signifies the $i^{th}$ element of the array.

The authentication application 116 also can determine additional morphological characteristics of the blood flow based on the waveform 1000 (and successive blood flow signals). For example, the authentication application 116 can determine an area 1030 under the curve of the waveform 1000 during the systolic phase between the time ($t_{t1}$) of a first trough 1020 and the time ($t_{sp}$) of the systolic peak 1005. The authentication application 116 also can determine and an area 1035 under the curve of the waveform 1000 during the diastolic phase between the time ($t_{sp}$) of the systolic peak 1005 and the time ($t_{t2}$) of a second trough 1025. The area 1030 under the curve can be indicative of the user's cardiac output in the systolic phase of heart beating. The area 1035 under the curve can be indicative of the user's cardiac output in the diastolic phase of heart beating. The authentication application 116 can generate parameters indicating the respective areas 1030, 1035 to represent morphological characteristics.

By way of example, the authentication application 116 can determine the area 1030 under the curve for the systolic phase using the following equation:

$$\frac{\text{abs}(t_{sp}[i, ppg1] - t_{t1}[i, ppg1])}{2|ppg1[t_{sp}[i, ppg1]:t_{t1}[i, ppg1]]|} \sum_{k=f_s \cdot t_{t1}[i, ppg1]}^{f_s \cdot t_{sp}[i, ppg1]} \text{abs}(ppg1[k+1] - ppg1[k])$$

where ppg1 is data contained in the sensor data 140, k is the sample number for digitized PPG signal value, i is the number of sensed (systolic and diastolic) phases to which a parameter pertains, and [i] signifies the $i^{th}$ element of the array. The area 1035 under the curve for the diastolic phase can be computed using the following equation:

$$\frac{\text{abs}(t_{t2}[i, ppg1] - t_{sp}[i, ppg1])}{2|ppg1[t_{t2}[i, ppg1]:t_{sp}[i, ppg1]]|} \sum_{k=f_s \cdot t_{sp}[i, ppg1]}^{f_s \cdot t_{t2}[i, ppg1]} \text{abs}(ppg1[k+1] - ppg1[k]).$$

The areas 1030, 1035 under the curve are morphological characteristics indicative of a user's cardiac output in the respective systolic and diastolic phases of the user's heart beating, and can correlate with respective blood flow volumes during the systolic and diastolic phases.

Also, from the series of waveforms, the authentication application 116 can determine the statistical characteristics of the waveforms. The statistical characteristics can indicate how successive waveforms change over time. For example, the authentication application 116 can determine a standard deviation of difference in peak times, an absolute difference in peak times, differences in numbers of detected extrema, etc. By way of example, the standard deviation of difference in peak times can be determined by the authentication application 116 using the following equation:

$$S_\Delta = \frac{\sum_{i=1}^{\min(|t_{sp}[:, ppg1]|, |t_{sp}[:, ppg2]|)} (\Delta t_{sp}[i] - \overline{\Delta t_{sp}})^2}{\min(|t_{sp}[:, ppg1]|, |t_{sp}[:, ppg2]|) - 1}$$

where $\Delta t_{sp}[i] = (t_{sp}[i, ppg1] - t_{sp}[i, ppg2])$, ppg1 is data contained in the sensor data 140 for a first PPG, ppg2 is data contained in the sensor data 142 for a second PPG, i is the number of sensed (systolic and diastolic) phases to which a parameter pertains, and [i] signifies the $i^{th}$ element of the array.

A difference (d) in a number of detected extrema times for various rise times $T_r$ can be determined by the authentication application 116 using the following equation:

$$d = ||t_{sp}[:, ppg1]| + |t_{t1}[:, ppg1]| - |t_{t1}[:, ppg2]| - |t_{sp}[:, ppg2]||.$$

The authentication application 116 also can determine heart flow signal correlation (C[g]), for example using the following equation:

$$C[g]ppg1 \otimes ppg2 = \sum_{m=0}^{N-1} ppg1[m]ppg2[g+m] \text{ for } g = [-N, N]$$

Where given a particular point "m" on the signal ppg1[m], the correlation with the PPG from the second source is being computed by signal points that lie inside a window centered on "m", and N wide on either side of "m". The authentication application 116 also can determine a maximum correlation (i.e. max(C)), and a cross-correlation value at no lag C[0]. Further, the authentication application 116 can determine a maximum lag (arg max $C_n[g]$) to match normalized signals with cross-correlation, where $C_n[g]$=ppg1/max(abs(ppg1)) $\otimes$ ppg2/max(abs(ppg2)).

The authentication application 116 also can determine a Euclidean distance between normalized signals using the following equation:

$$d(k) = \sum_{i=0}^{k} \sqrt{\left(\frac{ppg1[i]}{\max(\text{abs}(ppg1[0:k]))} - \frac{ppg2[i]}{\max(\text{abs}(ppg2[0:k]))}\right)^2}$$

Further, the authentication application 116 can determine variability in difference of normalized values of second derivatives of the PPG waveforms or acceleration PPG signal (APG), as well as higher-order statistics (HOSs).

Differencing operations can applied to the PPG signals near the end of the acquisition and verification period in order to obtain acceleration photoplethysmograph (APG) signals. Further, numerical differentiation can be applied to detrended PPG signals and the resulting APG signals. Variability among outputs which are the desired APG signals can be measured using a calculated ratio of the variance of the envelope of the difference signal relative to the absolute maximum of the difference signal.

SVM learning models can applied using the abovementioned features, for example as described with respect to FIG. 9. The SVM models can be developed a priori using vectors $\overline{x_i}$ containing values of features extracted from training data with associated $y_i$ equal to –1 or 1 for examples of users being different or the same respectively. Equations of the maximum margin decision boundary of the SVM classifiers can be determined, for example by solving the following equation:

$$\vec{w} \cdot \vec{x}_+ \vec{b} = 0$$

Determining the SVM classifiers in such manner can maximize the gap $(2/\|\vec{w}\|)$ between the hyperplane bounding feature values for training examples of users being different and the parallel hyperplane bounding feature values for training examples of the user being the same. Parameters can be numerically obtained using quadratic programming procedures which can minimize $(\frac{1}{2}\|\vec{w}\|^2 + C\Sigma_{i=1}^{n} z)$ subject to the constraint of correct classification of training examples (i.e., $y_i(\vec{w} \cdot \vec{x}_i + \vec{b}) \geq 1 - z_i$ for $i=1, \ldots N$). Optimization can be used to obtain the correlation parameter C as well as the subsets of features, and five-fold cross-validation can be invoked to confirm predictive capabilities. Verification of the user can be determined to be the majority vote on ensemble of the binary SVM model classifiers.

Figure 11:
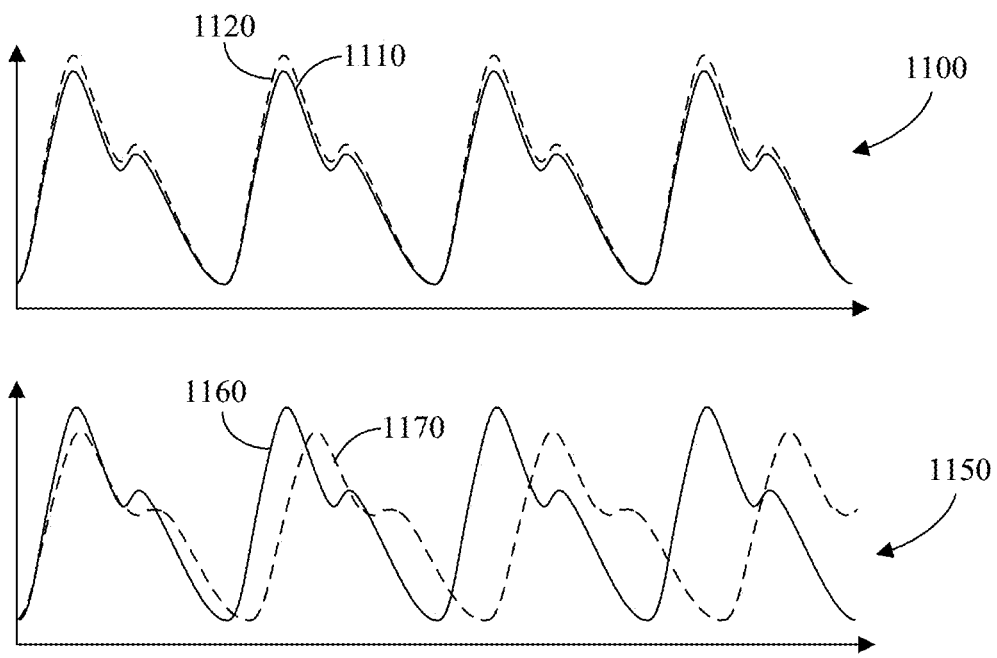
FIG. 11 depicts examples blood flow waveform comparisons.

FIG. 11 depicts examples blood flow waveform comparisons 1100, 1150. The blood flow waveform comparisons 1100, 1150 can be performed based on blood flow parameters derived from the blood flow waveforms, such as those previously described.

The blood flow waveform comparison 1100 can be based on respective parameters generated for a blood flow waveform 1110 and a blood flow waveform 1120. In this example, a threshold percentage of the parameters representing morphological characteristics, physiological biomarkers and/or statistical characteristics of the respective waveforms 1110, 1120 can be determined to match. In illustration, a threshold percentage of parameters representing the respective waveforms 1110, 1120 may be within a threshold value (e.g., threshold percentage) of each other. For instance, amplitudes of the respective diastolic peaks, systolic peaks and dicrotic notches may differ, but less than a threshold percentage for a threshold number (e.g., percentage) of such parameters. Further, values of times between the various peaks, systolic peaks, dicrotic notches and troughs may differ, but less than a threshold percentage for a threshold number (e.g., percentage) of such parameters. Similarly, parameters representing physiological biomarkers of the blood flow and/or statistical characteristics of the waveforms 1110, 1120 may not be exactly the same, but may be within a threshold percentage value of each other for a threshold number (e.g., percentage) of such parameters. Thus, the authentication application 116 can determine that the waveforms 1110, 1120 match, and thus were generated for the same user. Accordingly, the authentication application 116 can output an indicator to the pairing application 114 indicating that the user is authenticated.

In one aspect of the present arrangements, not all morphological characteristics, physiological biomarkers and statistical characteristics need to be within respective threshold values (e.g., threshold percentages) of one another in order to determine that the waveforms 1110, 1120 match. For example, the waveforms 1110, 1120 can be determined to match if a threshold percentage of the compared parameters match. In illustration, the waveforms 1110, 1120 can be determined to match if 70%, 75%, 80%, 85%, 90% or 95% of the parameters generated for the waveform 1110 match corresponding parameters generated for the waveform 1120.

The blood flow waveform comparison 1150 can be based on respective parameters generated for a blood flow waveform 1160 and a blood flow waveform 1170 that do not match. In this example, less than a threshold percentage of the parameters representing morphological characteristics, physiological biomarkers and/or statistical characteristics of the respective waveforms 1160, 1170 can be determined to match. Thus, the authentication application 116 can determine that the waveforms 1160, 1170 do not match, and thus were not generated for the same person. Accordingly, the authentication application 116 can output an indicator to the pairing application 114 indicating that the user is not authenticated.

Figure 12:
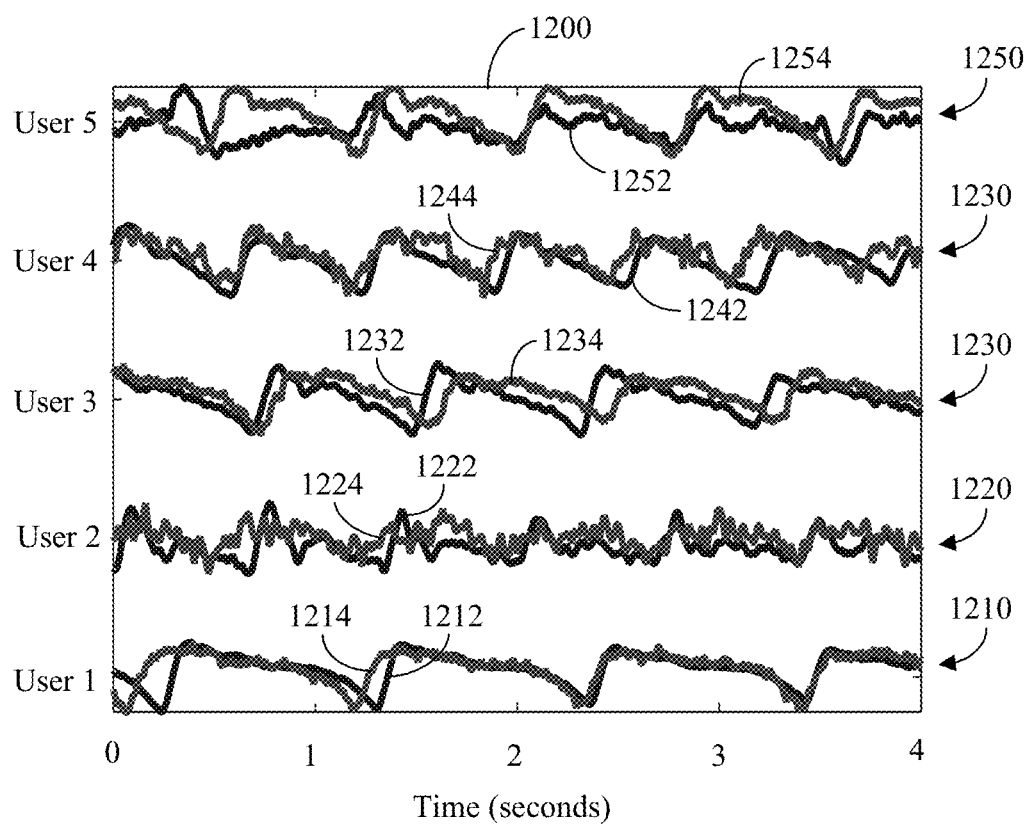
FIG. 12 is a chart depicting examples of blood flow waveform comparisons.

FIG. 12 is a chart 1200 depicting examples of blood flow waveform comparisons 1210, 1220, 1230, 1240, 1250 performed on various users, User 1, User 2, User 3, User 4 and User 5, during laboratory testing. The waveforms 1212, 1222, 1232, 1242, 1252 were generated for the respective users using a smart phone. The waveforms 1214, 1224, 1234, 1244, 1254 were generated for the respective users using a smart watch. Additional comparisons also were performed during the laboratory testing. Results from the laboratory testing confirmed that comparing blood flow waveforms in accordance with the arrangements described herein resulted in an accuracy for correctly authenticating a user in excess of 90%. Moreover, such accuracy was shown to result using approximately three seconds of measured blood flow data, though less time may used for certain features.

The terminology used herein is for the purpose of describing particular arrangements only and is not intended to be limiting. Notwithstanding, several definitions that apply throughout this document now will be presented.

Several definitions that apply throughout this document now will be presented.

As defined herein, the term "physiological biomarker" means a parameter indicating a physiologically functional characteristic (e.g., a heart rate, heart rate variability, oxygen saturation, arterial tone, aging index, etc.).

As defined herein, the term "morphological characteristic" means a shape of a blood flow signal. A physiological biomarker is not a "morphological characteristic" as the term "morphological characteristic" is defined herein.

As defined herein, the term "statistical characteristic of blood flow" means a characteristic of blood flow pattern that may be analyzed statistically but may not be predicted precisely.

As defined herein, the term "user device" means a processing system including at least one processor and memory with which a user directly interacts. Network infrastructure, such as routers, firewalls, switches, access points and the like, are not user devices as the term "user device" is defined herein.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory, as described herein, are examples of a computer readable storage medium. A non-exhaustive list of more specific examples of a computer readable storage medium may include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, or the like.

As defined herein, the term "processor" means at least one hardware circuit. The hardware circuit may be configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process.

As defined herein, the term "output" means storing in physical memory elements, e.g., devices, writing to display or other peripheral output device, sending or transmitting to another system, exporting, or the like.

As defined herein, the term "responsive to" means responding or reacting readily to an action or event. Thus, if a second action is performed "responsive to" a first action, there is a causal relationship between an occurrence of the first action and an occurrence of the second action, and the term "responsive to" indicates such causal relationship.

As defined herein, the term "user" means a human being.

As defined herein, the singular forms "a," "an," and "the" are intended to include the plural forms as well, unless the context clearly indicates otherwise. As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together. As defined herein, the term "automatically" means without user intervention.

As defined herein, the terms "one arrangement," "an arrangement," "one or more arrangements," or similar language mean that a particular feature, structure, or characteristic described in connection with the arrangement is included in at least one arrangement described within this disclosure. Thus, appearances of the phrases "in one arrangement," "in an arrangement," "in one or more arrangements" and similar language throughout this disclosure may, but do not necessarily, all refer to the same arrangement.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowchart or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

The corresponding structures, materials, acts, and equivalents of all means or step plus function elements that may be found in the claims below are intended to include any structure, material, or act for performing the function in combination with other claimed elements as specifically claimed.

The description of the arrangements provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the arrangements disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method of authenticating a user using a user device comprising:
   measuring, by the user device, using a first sensor, blood characteristics of the user and generating first sensor data based on the measuring of the blood characteristics;
   determining, based on the first sensor data, at least a first physiological biomarker of the blood characteristics measured by the first sensor, wherein the first physiological biomarker indicates a first oxygen saturation;
   deriving acceleration plethysmography parameters of the first sensor data;
   deriving at least a first morphological characteristic of the blood characteristics measured by the first sensor by processing the acceleration plethysmography parameters of the first sensor data;
   receiving second sensor data generated by a second sensor performing remote oximetry sensing, wherein the second sensor is remote to the user device;
   determining, based on the second sensor data, at least a second physiological biomarker of a blood flow detected by the second sensor, wherein the second physiological biomarker indicates a second oxygen saturation;
   receiving third sensor data generated by a third sensor, wherein the third sensor is remote to the user device;
   deriving acceleration plethysmography parameters of the third sensor data and deriving at least a second morphological characteristic of blood characteristics detected by the third sensor by processing the acceleration plethysmography parameters of the third sensor data;
   comparing the at least the first oxygen saturation to at least the second oxygen saturation and comparing at least the first morphological characteristic to at least the second morphological characteristic;
   determining whether at least the first oxygen saturation matches at least the second oxygen saturation and determining whether at least the first morphological characteristic matches at least the second morphological characteristic; and
   responsive to at least the first oxygen saturation matching at least the second oxygen saturation and at least the first morphological characteristic matching at least the second morphological characteristic, outputting an indicator indicating the user is authenticated.

2. The method of claim 1, wherein the second sensor data is received from the second sensor simultaneously with the first sensor data being measured by the first sensor.

3. The method of claim 1, wherein the first morphological characteristic of blood characteristics of the user indicate a cardiac output of the user in a systolic phase of blood flow or a diastolic phase of blood flow.

4. The method of claim 1, wherein the first morphological characteristic of blood characteristics of the user indicate a difference between a systolic peak of blood flow and a diastolic peak of blood flow, a difference between the systolic peak of blood flow and a dicrotic notch of blood flow, or a difference between the diastolic peak of blood flow and the dicrotic notch of blood flow.

5. The method of claim 3, further comprising:
   filtering the first sensor data by performing infinite impulse response (IIR) filtering on the first sensor data and performing de-trending filtering on the IIR filtered sensor data;
   wherein the first physiological biomarker of the blood characteristics measured by the first sensor is determined based on the filtered first sensor data.

6. A user device, comprising:
   a memory configured to store instructions;
   a processor coupled to the memory, wherein the processor, in response to executing the instructions, is configured to initiate operations for authenticating a user comprising:
   measuring, using a first sensor of the user device, blood characteristics of the user and generating first sensor data based on the measuring of the blood characteristics;
   determining, based on the first sensor data, at least a first physiological biomarker of the blood characteristics measured by the first sensor, wherein the first physiological biomarker indicates a first oxygen saturation;
deriving acceleration plethysmography parameters of the first sensor data;
deriving at least a first morphological characteristic of the blood characteristics by processing the acceleration plethysmography parameters of the first sensor data;
receiving second sensor data generated by a second sensor performing remote oximetry sensing, wherein the second sensor is remote to the user device;
determining, based on the second sensor data, at least a second physiological biomarker of a blood flow detected by the second sensor, wherein the second physiological biomarker indicates a second oxygen saturation;
receiving third sensor data generated by a third sensor, wherein the third sensor is remote to the user device;
deriving acceleration plethysmography parameters of the third sensor data and deriving at least a second morphological characteristic of blood characteristics detected by the third sensor by processing the acceleration plethysmography parameters of the third sensor data;
comparing the at least the first oxygen saturation to at least the second oxygen saturation and comparing at least the first morphological characteristic to at least the second morphological characteristic;
determining whether at least the first oxygen saturation matches at least the second oxygen saturation and determining whether at least the first morphological characteristic matches at least the second morphological characteristic; and
responsive to at least the first oxygen saturation matching at least the second oxygen saturation and at least the first morphological characteristic matching at least the second morphological characteristic, outputting an indicator indicating the user is authenticated.

7. The user device of claim 6, wherein the second sensor data is received from the second sensor simultaneously with the first sensor data being measured by the first sensor.

8. The user device of claim 6, wherein the first morphological characteristic of blood characteristics of the user indicate a cardiac output of the user in a systolic phase of blood flow or a diastolic phase of blood flow.

9. The user device of claim 8, the operations further comprising:
filtering the first sensor data by performing infinite impulse response (IIR) filtering on the first sensor data and performing de-trending filtering on the IIR filtered sensor data;
wherein the first physiological biomarker of the blood characteristics measured by the first sensor is determined based on the filtered first sensor data.

10. The user device of claim 6, wherein the first morphological characteristic of blood characteristics of the user indicate a difference between a systolic peak of blood flow and a diastolic peak of blood flow, a difference between the systolic peak of blood flow and a dicrotic notch of blood flow, or a difference between the diastolic peak of blood flow and the dicrotic notch of blood flow.

11. A computer program product comprising a computer readable storage medium having program code stored thereon for authenticating a user, the program code executable by a processor of a user device to perform operations comprising:

measuring, by the user device, using a first sensor, blood characteristics of the user and generating first sensor data based on the measuring of the blood characteristics;
determining, based on the first sensor data, at least a first physiological biomarker of the blood characteristics measured by the first sensor, wherein the first physiological biomarker indicates a first oxygen saturation;
deriving acceleration plethysmography parameters of the first sensor data;
deriving at least a first morphological characteristic of the blood characteristics by processing the acceleration plethysmography parameters of the first sensor data;
receiving second sensor data generated by a second sensor performing remote oximetry sensing, wherein the second sensor is remote to the user device;
determining, based on the second sensor data, at least a second physiological biomarker of a blood flow detected by the second sensor, wherein the second physiological biomarker indicates a second oxygen saturation;
receiving third sensor data generated by a third sensor, wherein the third sensor is remote to the user device;
deriving acceleration plethysmography parameters of the third sensor data and deriving at least a second morphological characteristic of blood characteristics detected by the third sensor by processing the acceleration plethysmography parameters of the third sensor data;
comparing the at least the first oxygen saturation to at least the second oxygen saturation and comparing at least the first morphological characteristic to at least the second morphological characteristic;
determining whether at least the first oxygen saturation matches at least the second oxygen saturation and determining whether at least the first morphological characteristic matches at least the second morphological characteristic; and
responsive to at least the first oxygen saturation matching at least the second oxygen saturation and at least the first morphological characteristic matching at least the second morphological characteristic, outputting an indicator indicating the user is authenticated.

12. The computer program product of claim 11, wherein the second sensor data is received from the second sensor simultaneously with the first sensor data being measured by the first sensor.

13. The computer program product of claim 11, wherein the first morphological characteristic of blood characteristics of the user indicate a cardiac output of the user in a systolic phase of blood flow or a diastolic phase of blood flow.

14. The computer program product of claim 13, the operations further comprising:
filtering the first sensor data by performing infinite impulse response (IIR) filtering on the first sensor data and performing de-trending filtering on the IIR filtered sensor data;
wherein the first physiological biomarker of the blood characteristics measured by the first sensor is determined based on the filtered first sensor data.

15. The computer program product of claim 11, wherein the first morphological characteristic of blood characteristics of the user indicate a difference between a systolic peak of blood flow and a diastolic peak of blood flow, a difference between the systolic peak of blood flow and a dicrotic notch of blood flow, or a difference between the diastolic peak of blood flow and the dicrotic notch of blood flow.

\* \* \* \* \*